United States Patent
Bin et al.

(10) Patent No.: US 9,123,900 B2
(45) Date of Patent: Sep. 1, 2015

(54) HOST MATERIAL AND ORGANIC LIGHT EMITTING DISPLAY DEVICE USING THE SAME

(71) Applicant: LG DISPLAY CO., LTD., Seoul (KR)

(72) Inventors: Jong Kwan Bin, Gyeonggi-do (KR); In Bum Song, Seoul (KR); Jung Keun Kim, Seoul (KR); Nam Sung Cho, Daejeon (KR); Bang Sook Lee, Seoul (KR); Suk Young Bae, Seoul (KR); Young Ju Ryu, Busan (KR)

(73) Assignee: LG Display Co., Ltd., Seoul (KR)

( * ) Notice: Subject to any disclaimer, the term of this patent is extended or adjusted under 35 U.S.C. 154(b) by 350 days.

(21) Appl. No.: 13/688,479

(22) Filed: Nov. 29, 2012

(65) Prior Publication Data
US 2013/0140539 A1 Jun. 6, 2013

(30) Foreign Application Priority Data
Dec. 6, 2011 (KR) .......................... 10-2011-0129902

(51) Int. Cl.
*H01L 51/50* (2006.01)
*H01L 51/00* (2006.01)
*C07F 7/10* (2006.01)

(52) U.S. Cl.
CPC .............. *H01L 51/0072* (2013.01); *C07F 7/10* (2013.01); *H01L 51/0071* (2013.01); *H01L 51/0094* (2013.01); *H01L 51/5092* (2013.01); *H01L 51/5016* (2013.01)

(58) Field of Classification Search
None
See application file for complete search history.

(56) References Cited

FOREIGN PATENT DOCUMENTS

JP 2001-278889 * 10/2001 ............. C09K 11/06
JP 2001-278889 A 10/2001

OTHER PUBLICATIONS

Office Action issued in counterpart Korean Patent Application No. 10-2011-0129902 dated Aug. 31, 2014.

* cited by examiner

*Primary Examiner* — Gregory Clark
(74) *Attorney, Agent, or Firm* — Morgan, Lewis & Bockius LLP

(57) ABSTRACT

A host material is disclosed. The host material, as a compound which is represented by the following formula 1, has a chemical structure in which nitrogen and silicon atoms are chemically and directly bonded to each other.

[Formula 1]

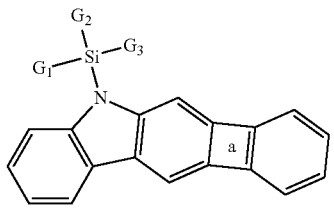

Wherein the "a" is one selected from a material group which includes N, S, O, $SO_2$ and $NSiG_1G_2G_3$, and the "G1, G2 and G3" each become one of a hydrogen, and aromatic, heterocyclic and aliphatic groups which are or not substituted, respectively.

10 Claims, 2 Drawing Sheets

HOST MATERIAL AND ORGANIC LIGHT EMITTING DISPLAY DEVICE USING THE SAME

The present application claims priority under 35 U.S.C. §119(a) of Korean Patent Application No. 10-2011-0129902 filed on Dec. 6, 2011, which is hereby incorporated by reference in its entirety.

BACKGROUND

1. Field of the Disclosure

The present application relates to an organic light emitting display device, and more particularly to a host material and an organic light emitting display device that are adapted to enhance efficiency and lifespan.

2. Description of the Related Art

Nowadays, as the information society grows, display devices have been rapidly developed. Among the display devices, OLED devices are a self-illuminating display device not requiring a backlight unit. As such, the OLED devices can become thinner. Also, the OLED devices can have low power consumption.

The organic light emitting display device includes an anode electrode, a cathode electrode and a light emission layer interposed between the anode and cathode electrodes. The anode electrode applies holes to the light emission layer, and the cathode electrode applies electrons to the light emission layer. In accordance therewith, excitons are generated in the light emission layer through the recombination of electrons and holes. The exciton emits light in transition to the ground state.

The excitons can be classified into singlet and triplet excitons. The singlet and triplet excitons exist in a ratio of 1:3. In order to emit light, fluorescence uses only the singlet excitons but phosphorescence uses both the singlet and triplet excitons. As such, the organic light emitting display device using a phosphorescent material can have a higher luminous efficiency compared to that using a fluorescent material. In other words, the phosphorescent material having higher quantum efficiency than that of the fluorescent material can increase the luminous efficiency of the organic light emitting display device. In view of this point, a variety of phosphorescent materials to be used in the organic light emitting display device are being researched.

The phosphorescent materials each include a host material and a phosphorescent dopant material capable of emitting light using the transition energy from the host material. In order to generate an energy transition phenomenon without causing a backward energy transition, a triple energy level of the phosphorescent dopant must be sufficiently greater than that of the host material. On the contrary, when the triplet energy level of the host material is higher than that of the phosphorescent dopant, the quantum efficiency of the host material cannot be maximized.

However, the triplet energy level of the host material according to the related art is lower than that of the phosphorescent dopant. Due to this, the quantum efficiency of the host material cannot be enhanced without limit.

Also, the related art host material has a low glass transition temperature. As such, the host material must be affected in thermal stability. Furthermore, the host material can be easily deformed at a high temperature or a driving temperature. As a result, the life span of a device including the host material can be reduced.

In view of these points, it is necessary to develop new host materials which are adapted to enhance the luminous efficiency and the life span of the organic light emitting display device.

BRIEF SUMMARY

Accordingly, embodiments of the present application are directed to a host material that substantially obviates one or more of problems due to the limitations and disadvantages of the related art, and to an organic light emitting display device using the same.

The embodiments are to provide a host material capable of simultaneously enhancing the luminous efficiency and the life span, as well as an organic light emitting display device using the same.

Additional features and advantages of the embodiments will be set forth in the description which follows, and in part will be apparent from the description, or may be learned by practice of the embodiments. The advantages of the embodiments will be realized and attained by the structure particularly pointed out in the written description and claims hereof as well as the appended drawings.

A host material according to a general aspect of the present embodiment is provided as a solution to the above-mentioned problems. The host material corresponding to a compound which is represented by the following formula 1, and having a chemical structure in which nitrogen and silicon atoms are chemically and directly bonded to each other.

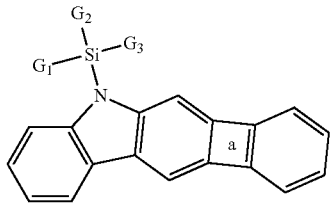

[Formula 1]

Wherein the "a" is one selected from a material group which includes N, S, O, $SO_2$ and $NSiG_1G_2G_3$, and the "G1, G2 and G3" each become one of a hydrogen, and aromatic, heterocyclic and aliphatic groups which are or not substituted, respectively.

An organic light emitting display device according to another general aspect of the present embodiment is provided as another solution to the above-mentioned problems. The organic light emitting display device includes a light emission layer which is interposed between an anode and a cathode. The light emission layer includes a dopant material and a host material represented by the following formula 1.

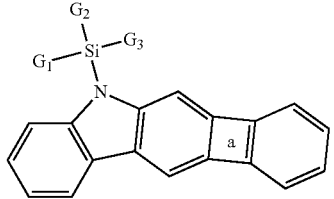

[Formula 1]

Wherein the "a" is one selected from a material group which includes N, S, O, $SO_2$ and $NSiG_1G_2G_3$, and the "G1, G2 and G3" each become one of a hydrogen, and aromatic, heterocyclic and aliphatic groups which are or not substituted, respectively.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments. It is to be understood that both the foregoing general description and the following detailed description of the present disclosure are exemplary and explanatory and are intended to provide further explanation of the disclosure as claimed.

BRIEF DESCRIPTION OF THE DRAWINGS

The accompanying drawings, which are included to provide a further understanding of the embodiments and are incorporated herein and constitute a part of this application, illustrate embodiment(s) of the present disclosure and together with the description serve to explain the disclosure. In the drawings.

DETAILED DESCRIPTION OF THE EMBODIMENTS

Figure 1:
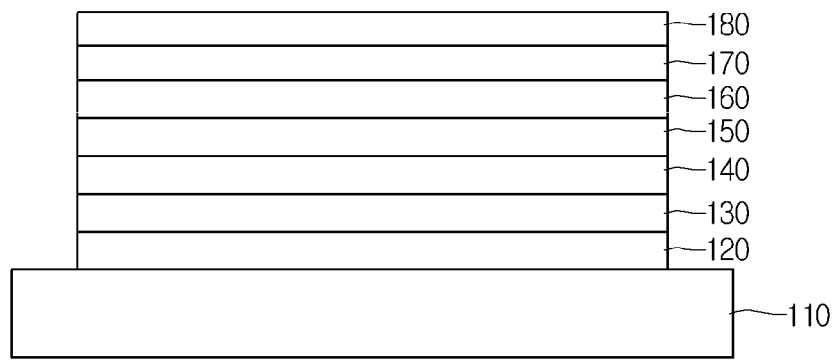
FIG. 1 is a cross-sectional view showing an organic light emitting display device according to an embodiment of the present disclosure.

First, a host material according to a first embodiment of the present disclosure will be described.

The host material of the first embodiment can be represented by the following formula 1.

[Formula 1]

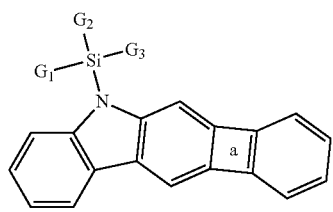

In the formula 1, "a" can become one selected from a material group which includes N, S, O, $SO_2$ and $NSiG_1G_2G_3$. In other words, the compound represented by the formula 1 can become one of compounds being represented by the following formulas A1 through A10. However, the present embodiment is not limited to these.

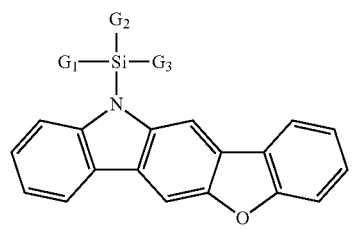

A1

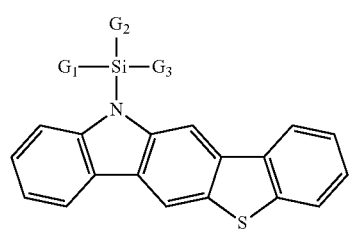

A2

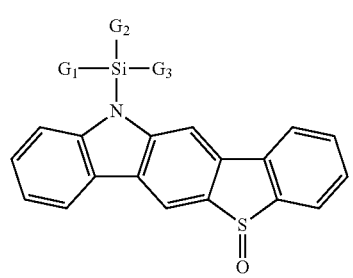

A3

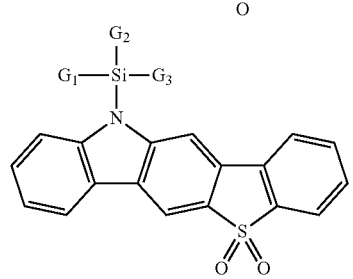

A4

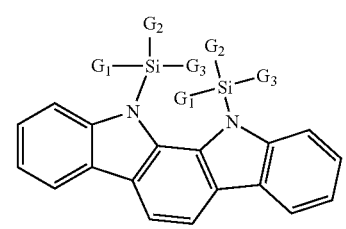

A5

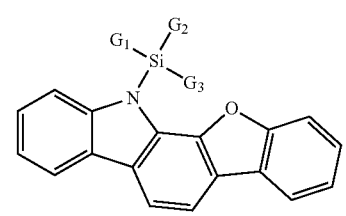

A6

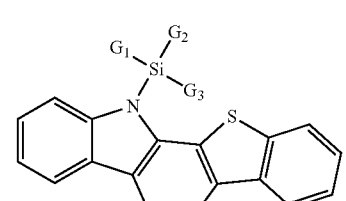

A7

A8
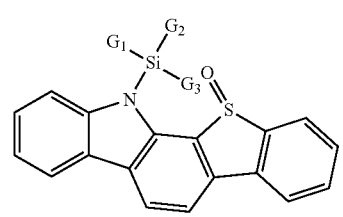

A9
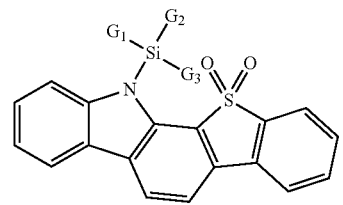

A10
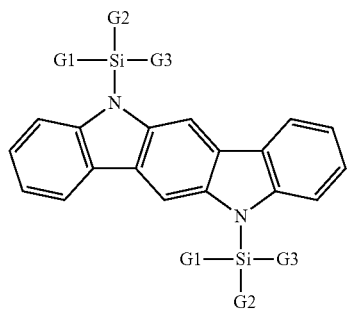

In the compound represented by one of the formulas 1 and A1 through A10, the G1, G2 and G3 can each become one of hydrogen, and aromatic, heterocyclic and aliphatic groups which are or not substituted. In other words, G1, G2 and G3 may be either the same compound or different compounds.

A substitute capable of being substituted into the aromatic or heterocyclic group can include at least one among an alkyl group, an alkoxy group, a halogen group, a silyl group, a cyano group, deuterium, tritium and hydrogen.

The heterocyclic group can include 4 through 16 carbon atoms and at least one of one through three nitrogen atoms, one or two oxygen atoms and one or two sulfide atoms.

In detail, G1, G2 and G3 can be represented by one of the following formulas B1 through B64, respectively. As such, G1, G2 and G3 are the same as or different from one another.

B1
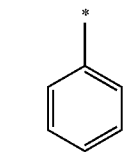

B2
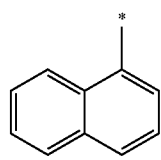

B3
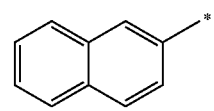

B4
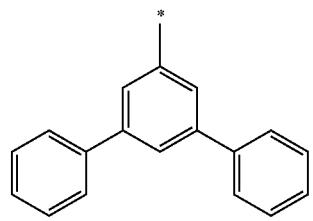

B5
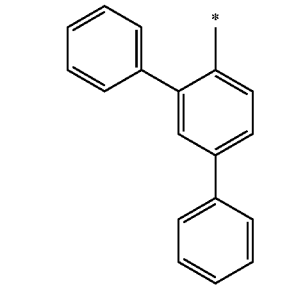

B6
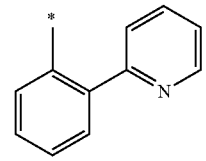

B7
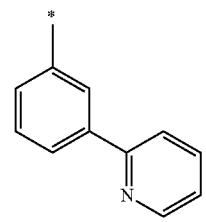

B8
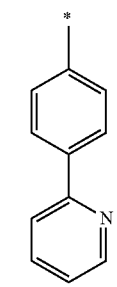

B9
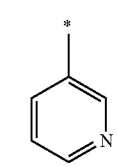

B10
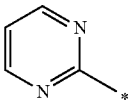

| | |
|---|---|
| B11 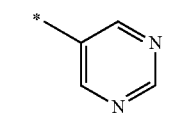 | B21 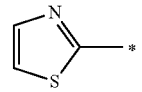 |
| B12 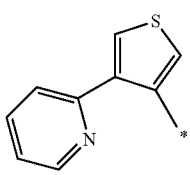 | B22 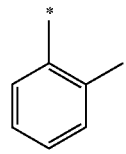 |
| B13 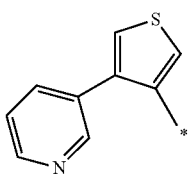 | B23 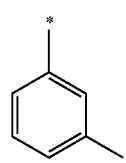 |
| B14 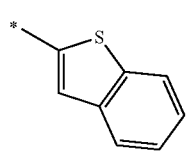 | B24 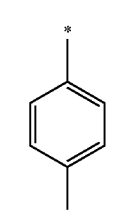 |
| B15 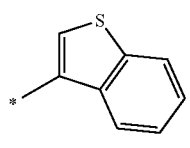 | B25 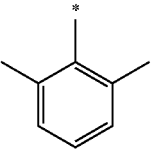 |
| B16 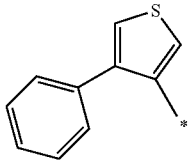 | B26 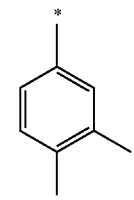 |
| B17 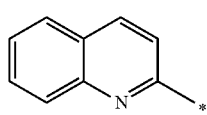 | B27 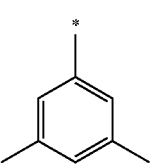 |
| B18 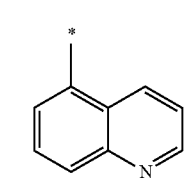 | B28 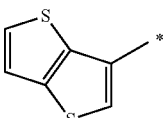 |
| B19 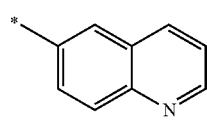 | B29 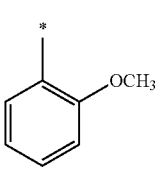 |
| B20 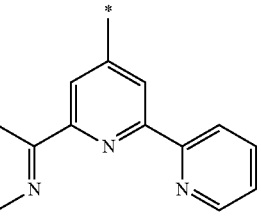 | |

| | |
|---|---|
| 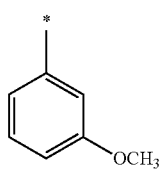 B30 | 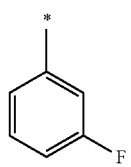 B39 |
| 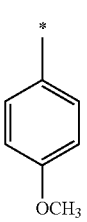 B31 | 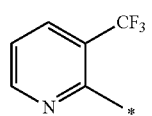 B40 |
| 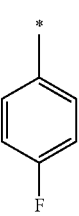 B32 | 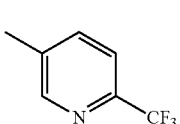 B41 |
| 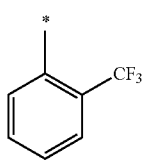 B33 | 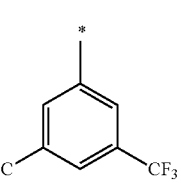 B42 |
| 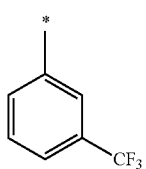 B34 | 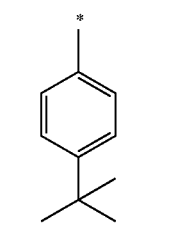 B43 |
| 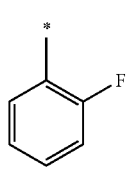 B35 | 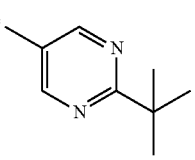 B44 |
| 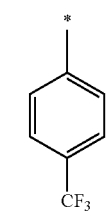 B36 | 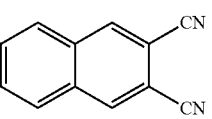 B45 |
| 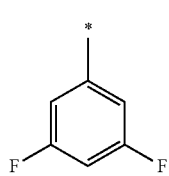 B37 |  B46 |
| | 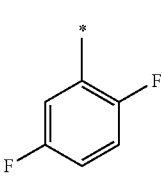 B47 |

B48 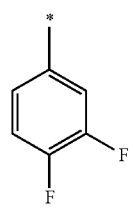
B49 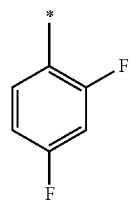
B50 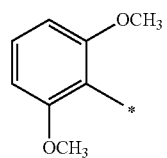
B51 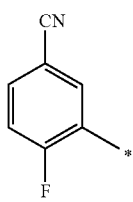
B52 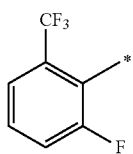
B53 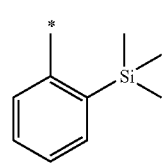
B54 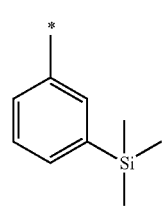
B55 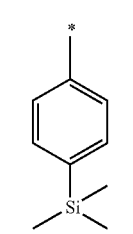
B56 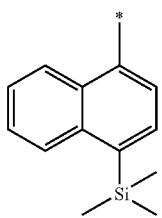
B57 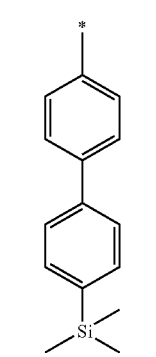
B58 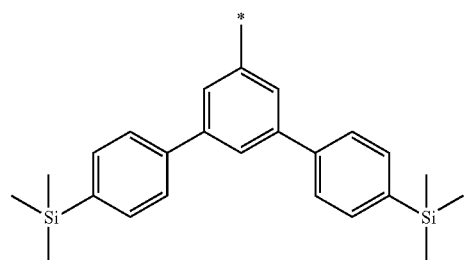
B59 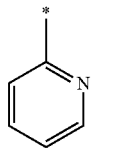
B60 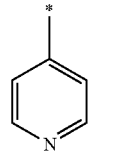
B61 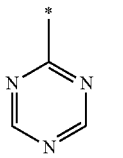
B62 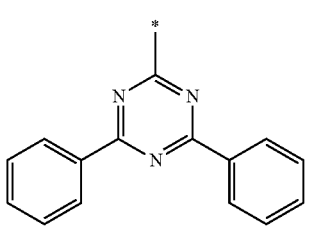

B63

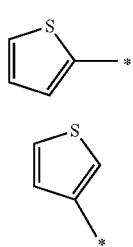

B64

In the formulas B1 through B64, "*" is a connection portion which is connected to another compound.

As represented by the formula 1, the host material has a chemical structure in which indolofluorene becomes an essential ingredient. In the host material, nitrogen N of indolofluorene is chemically and directly bonded with silicon of the substitution group. As such, the host material of the present embodiment can have a triplet energy level higher than that of the related art host material such as a CBP material. Therefore, the host material according to an embodiment of the present disclosure can become easier to transfer energy to the dopant, compared to the related art host material.

Also, the host material has a chemical structure which includes carbazole with a hole-donating property and a silyl group with an electron-donating property, as represented by the formula 1. As such, the host material can have bipolarity and maintain the numberical balance between holes and electrons. Therefore, it is not necessary for the host material to add a hole blocking layer and an electron blocking layer.

Moreover, the host material has the chemical structure which includes aromatic and silyl groups such as indolofluorene, represented by the formula 1. In accordance therewith, the host material of the present embodiment can have a higher glass transition temperature compared to the related art host material.

Reference regarding an organic light emitting display device will now be made in detail to the embodiments of the present disclosure, examples of which are illustrated in the accompanying drawings. These embodiments introduced hereinafter are provided as examples in order to convey their spirits to the ordinary skilled person in the art. Therefore, these embodiments might be embodied in a different shape, so are not limited to these embodiments described here. In the drawings, the size, thickness and so on of a device can be exaggerated for convenience of explanation. Wherever possible, the same reference numbers will be used throughout this disclosure including the drawings to refer to the same or like parts.

FIG. 1 is a cross-sectional view showing an organic light emitting display device according to a second embodiment of the present disclosure.

Referring to FIG. 1, the organic light emitting display device 100 according to an embodiment of the present disclosure can include an anode 120, a light emission layer 150 and a cathode 180 which are sequentially disposed on a substrate 110.

A material used to form the substrate 110 can be one of glass and a resin. If the substrate 110 is formed from a resin, the resin can become a material which has a lower rate of moisture or oxygen intrusion into the light emission layer 150 compared to the other materials. As an example of the resin, polycarbonate, polyimide, polyethylene terephthalate, polyethylene naphthalate and so on can be used. The substrate can be rigid or flexible.

The anode 120 is directly disposed on the substrate 110. Also, the anode 120 can be formed from a transparent conductive material. For example, the anode 120 can be from one of indium-tin-oxide ITO and indium-zinc-oxide IZO.

The light emission layer 150 is disposed on the anode 120. Also, the light emission layer 150 can be from a material emitting either green light or blue light.

If the light emission layer 150 emits blue light, the light emission layer can include a blue phosphorescent host material doped with a blue phosphorescent dopant. As an example of the blue phosphorescent dopant, an organometallic complex including one of iridium Ir, platinum Pt and europium Eu can be used. However, the present embodiment is not limited to the above-mentioned blue phosphorescent dopant material.

Such a blue phosphorescent host material can be represented by the following formula 1.

[Formula 1]

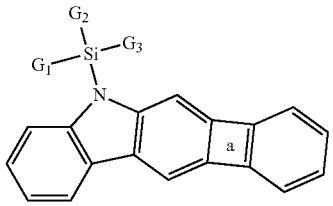

In detail, the blue phosphorescent host material represented by the formula 1 can become one of compounds being represented by the above-mentioned formulas A1 through A10.

In the compounds represented by the formulas 1 and A1 through A10, the terms of G1, G2 and G3 can each become one of hydrogen, and aromatic, heterocyclic and aliphatic groups which are or not substituted. In other words, G1, G2 and G3 can be either the same compound or different compounds from one another.

A substitute capable of being substituted into the aromatic or heterocyclic compound can include at least one among an alkyl group, an alkoxy group, a halogen group, a silyl group, a cyano group, deuterium, tritium and hydrogen.

The heterocyclic group can include 4 through 16 carbon atoms C and at least one of one through three nitrogen atoms N, one or two oxygen atoms O and one or two sulfide atoms S.

In detail, G1, G2 and G3 can be represented by one of the above-mentioned formulas B1 through B64, respectively. As such, G1, G2 and G3 are the same as or different from one another.

Meanwhile, when the light emission layer 150 emits green light, the light emission layer 150 can include a green phosphorescent host material doped with a green phosphorescent dopant.

The green phosphorescent dopant can be an organometallic complex including one of iridium Ir, platinum Pt and europium Eu. However, the present embodiment is not limited to this green phosphorescent dopant material.

The green phosphorescent host material can be represented by the above-mentioned formula 1. In other words, the blue and green phosphorescent materials can be represented by the above-mentioned formula 1. As such, the blue and green phosphorescent materials can be formed from the same compound or different compounds from each other.

Although it is explained that the light emission layer 150 is one of the blue and green light emission layers, the light emission layer 150 according to the present embodiment can include red, green and blue light emission layers separated from one another. In this case, the red, green and blue light emission layers are used to form a single pixel, so that display a variety of colors can be displayed.

The red light emission layer can include a red phosphorescent host material, such as "4,4'-N,N'-dicarbazole-biphenyl; CBP", doped with a red phosphorescent dopant such as bis (2-phenylquinoline)(acetylacetonate)iridium; Ir(Phq)2 (acac)). However, an embodiment of the present disclosure is not limited to this red light emission layer material.

The cathode 180 is disposed on the light emission layer 150. The cathode 180 can be formed from a reflective conductive material. For example, the cathode 180 can be from one of aluminum Al, silver Ag, chromium Cr, gold Au, tungsten W, titanium Ti and alloys thereof. However, an embodiment of the present embodiment is not limited to these cathode materials.

Also, the organic light emitting display device 100 can include at least one of a hole injection layer 130 and a hole transport layer 140 which are interposed between the anode 120 and the light emission layer 150.

The hole injection layer 130 can be disposed on the anode 120. Also, the hole injection layer 130 can induce the holes to be emitted from the anode 120. Such a hole injection layer 130 can be formed from "4,4'-bis[4-{{N,N-bis(3-methylphenyl)amino}phenyl}-N-phenylamino]biphenyl; DNTPD", as an example. However, the hole injection layer 130 is not limited to this material. Alternatively, the hole injection layer 130 can be formed from one of "4,4',4''-tris(3-methylphenyl-N-phenylamino)triphenylamine; m-MTDATA", "copper phthalocyanine; Cupc" and so on. The hole injection layer 130 can be formed using a vapor deposition method.

The hole transport layer 140 is used to smoothly transport the holes from the anode 120 to the light emission layer 150. As such, the hole transport layer 140 can prevent electron leakage from the light emission layer 150. Such a hole transport layer 140 can be formed from "N,N'-bis(naphthalene-1-yl)phenyl-N,N-bis(phenyl)-benzidine; NPB", as an example.

The hole injection layer 130 and the hole transport layer 140 are included the organic light emitting display device 100. In this case, the hole injection layer 130 and the hole transport layer 140 can be sequentially stacked on the anode 120.

The organic light emitting display device 100 can further include at one of an electron transport layer 160 and an electron injection layer 170 which are interposed between the light emission layer 150 and the cathode 180.

The electron transport layer 160 is used to smoothly transport the electrons emitted from the cathode 180 to the light emission layer 150. As such, the electron transport layer 160 can prevent hole leakage from the light emission layer 150 to the cathode 180. Such an electron transport layer 160 can be formed from one of "tris-8-hydroxyquinolinato aluminum; Alq3", "2-(4-biphenyl)-5-(4-tert-butylphenyl)-1,3,4-oxadiazole; PBD" and so on.

The electron injection layer 170 can induce the electrons to be emitted from the cathode 180. For example, the electron injection layer 170 can be formed from lithium fluoride.

In this manner, the organic light emitting display device 100 according to an embodiment of the present disclosure includes at least one of the hole and electron injection layers 130 and 170 and the hole and electron transport layers 140 and 160, as well as the light emission layer 150. In accordance therewith, the luminous efficiency and the life span of the organic light emitting display device 100 can be enhanced.

Also, the blue phosphorescent compound can be doped into at least one of the hole and electron injection layers 130 and 170, the light emission layer 150 and the hole and electron transport layers 140 and 160. As such, the organic light emitting display device 100 can enables electric charges to smoothly move.

Moreover, although it is not shown in the drawing, the organic light emitting display device 100 can include a sealing member configured to seal the anode 120, the light emission layer 150 and the cathode 180. The sealing member can shield the anode 120, the light emission layer 150 and the cathode 180 from the exterior. This results from the fact that the light emission layer 150 is easily deteriorated by external moisture or oxygen. Such a sealing member can become an upper substrate which is combined with the above-mentioned substrate 110 in such a manner as to face the substrate 110 with having the anode 120, the light emission layer 150 and the cathode 180 therebetween. Alternatively, the sealing member can become an inorganic insulation film formed to cover the substrate 110 provided with the anode 120, the light emission layer 150 and the cathode 180.

According to an embodiment of the present disclosure, the organic light emitting display device includes a new host material having a triplet energy level higher than that of the related art host material. Therefore, the luminous efficiency of the organic light emitting display device can be enhanced.

Also, the new host material can have bipolarity. As such, the leakage of holes and/or electrons from the light emission layer 150 can be prevented. Therefore, it is not necessary for the organic light emitting display device to add a hole blocking layer and/or an electron blocking layer.

Moreover, the new host material can have a higher glass transition temperature compared to the related art host material. As such, the deformation of the new host material due to heat at a high temperature or a driving temperature can be prevented. In accordance therewith, the organic light emitting display device can have a greatly lengthened life span compared to that of the related art.

Subsequently, a method of manufacturing a host material according to embodiments of the present disclosure will be explained in detail below through experimental examples. The experimental examples below are only used to explain the present embodiment. As such, the present embodiment is not limited to the experimental examples below.

EXPERIMENTAL EXAMPLE 1

Synthesis of indolo(3,2-b)carbazole

Under a nitrogen gas stream, about 250.69 g (i.e., about 205.8 mmol) of 3,3'-methylenediindole and about 30.55 g (i.e., about 206.1 mmol) of triethyl orthofomate are dissolved and mixed in methanol within a 3-neck flask. Thereafter, about 5.0 g (i.e., 51.5 mmol) of enriched sulfuric acid is slowly added little by little into the 3-neck flask and then the mixture within the 3-neck flask is refluxed during a single hour. The mixture within the 3-neck flask is frozen to be a normal temperature. Subsequently, about 33 g of indolo(3,2-b)carbazole corresponding to a compound of dark brown is obtained by filtering the frozen mixture.

The mechanism for the synthesis of indolo(3,2-b)carbazole can be represented by the following reaction equation 1.

[Reacton equation 1]

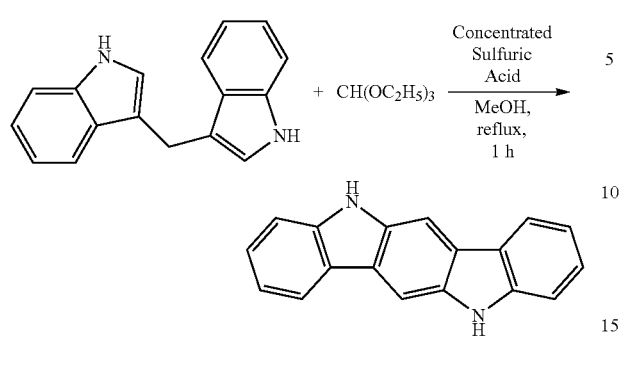

EXPERIMENTAL EXAMPLE 2

Synthesis of Host Material (PBH1)

About 2.0 g (corresponding to 7.8 mmol) of indolo(3,2-b) carbazole synthesized through the experimental example 1 is dissolved in about 100 ml of tetrahydrofuran THF within a 2-neck flask. Also, 17.20 mmol of 2.5M n-butyllithium (n-BuLi) is slowly added little by little into the solution in which indolo(3,2-b)carbazole is dissolved. Subsequently, the solution within the 2-neck flask is stirred during two hours before about 15.75 g (corresponding to 19.5 mmol) of triphenylchlorosilane is slowly added little by little into the tetrahydrofuran THF provided the dissolved reaction material at a temperature of 78° C. Then, the tetrahydrofuran THF in which the reaction materials are dissolved is stirred during six hours. A re-crystallization process using water and dichloromethane and a filtering process are sequentially performed for the tetrahydrofuran THF provided with the reaction materials, in order to obtain about 3.8 g of a new host material corresponding to PBH1. The yield ratio of the host material to the reaction materials corresponds to 63%.

The mechanism for the synthesis of the host material PBH1 can be represented by the following reaction equation 2.

[Reaction equation 2]

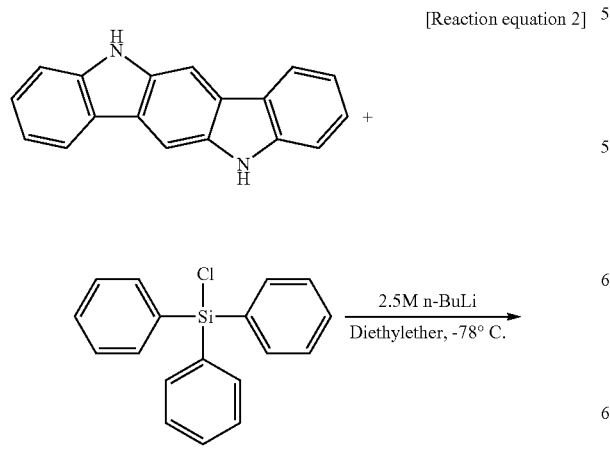

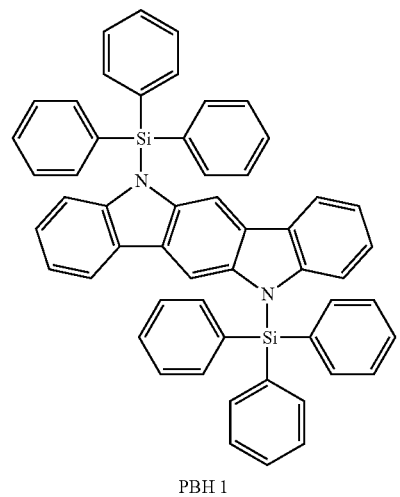

PBH 1

Figure 2:
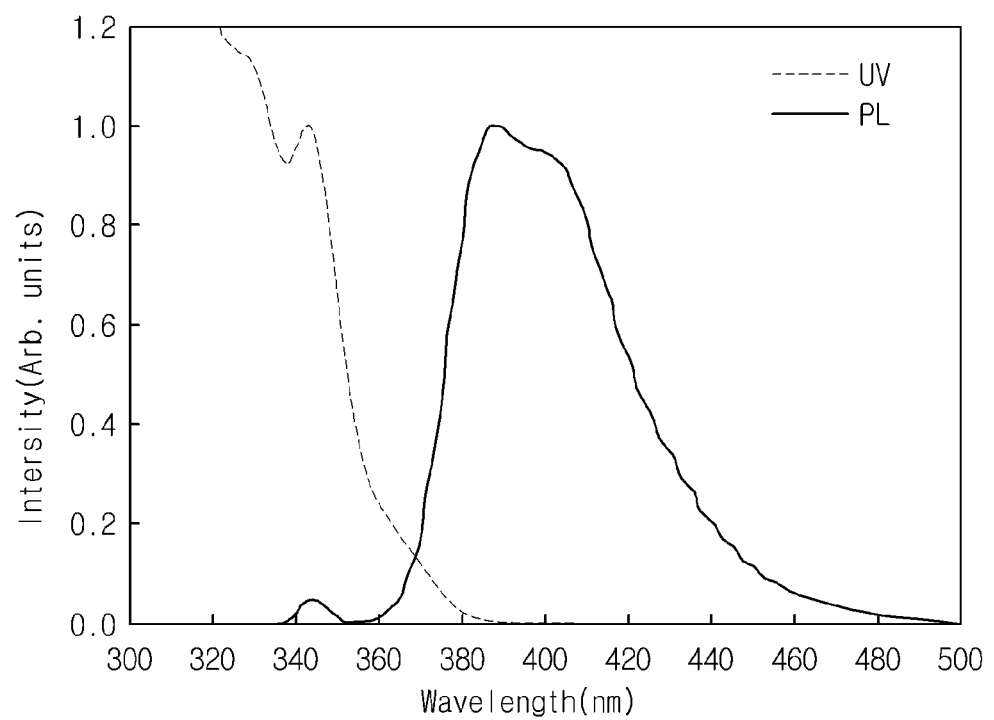
FIG. 2 is a graphic diagram illustrating UV and PL spectra of a host material according to an embodiment of the present disclosure.
Figure 3:
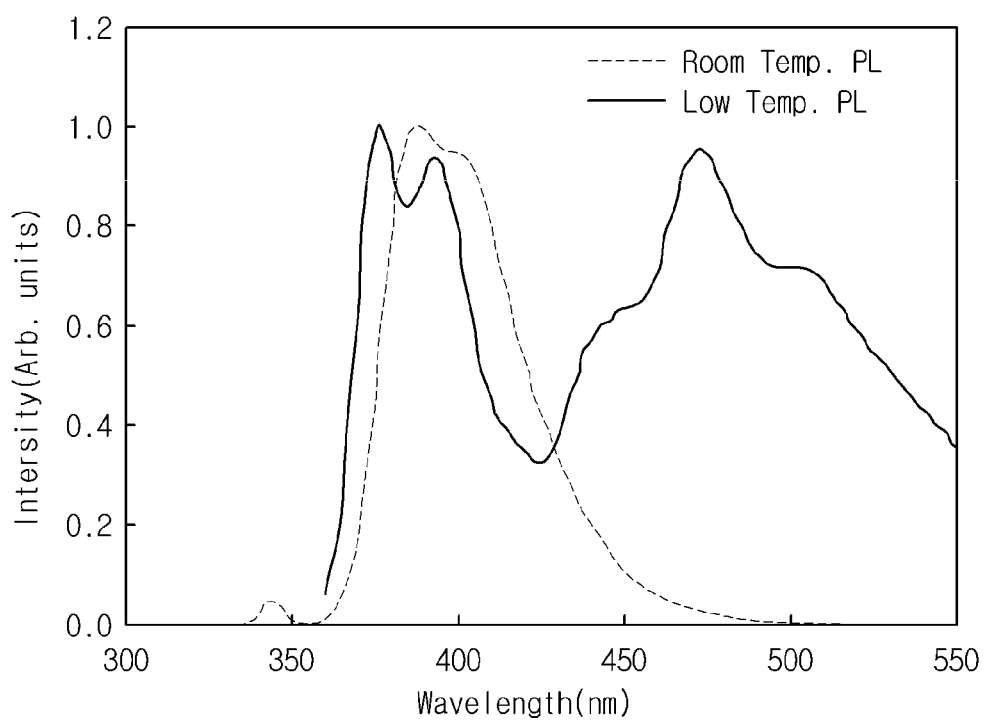
FIG. 3 is a graphic diagram illustrating low-temperature and normal-temperature PL spectra of a host material according to an embodiment of the present disclosure.

Table 1 and FIGS. 2 and 3 illustrate test resultants regarding the host material which is obtained through the experimental example 2.

TABLE 1

| Items | Wavelength(nm) | Energy(eV) |
|---|---|---|
| Excitation Wavelength | 344 | |
| Energy Bandgap(S1) | 380 | 3.26 |
| Triplet Energy(T1) | 450 | 2.76 |

FIG. 2 is a graphic diagram illustrating UV and PL spectra of a host material according to an embodiment of the present disclosure. FIG. 3 is a graphic diagram illustrating low-temperature and normal-temperature PL spectra of a host material according to an embodiment of the present disclosure. In FIG. 3, the low temperature is set to be 77K.

As seen from table 1 and FIGS. 2 and 3, it is evident that the host material obtained through the experimental example 2 has a triplet energy level of 2.76 eV. In other words, it can be confirmed that the host material obtained through the experiment example 2 has a higher triplet energy level compared to the related art host material, such as CBP, with the triplet energy level of 2.6 eV.

Although the present disclosure has been limitedly explained regarding only the embodiments described above, it should be understood by the ordinary skilled person in the art that the present disclosure is not limited to these embodiments, but rather that various changes or modifications thereof are possible without departing from the spirit of the present disclosure. Accordingly, the scope of the present disclosure shall be determined only by the appended claims and their equivalents.

What is claimed is:

1. A host material which is a compound represented by the following formulae:

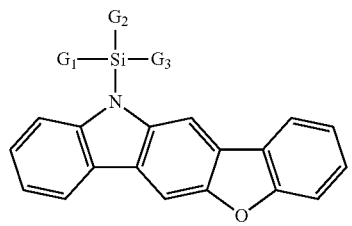
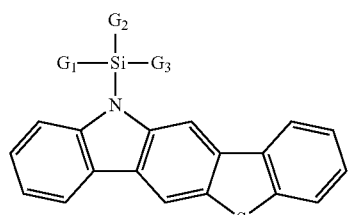
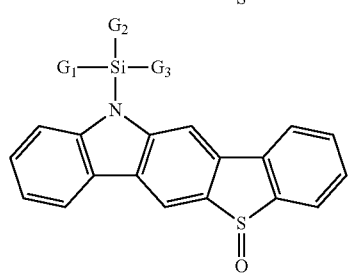
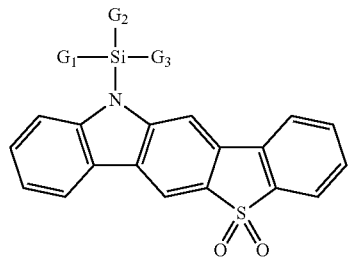
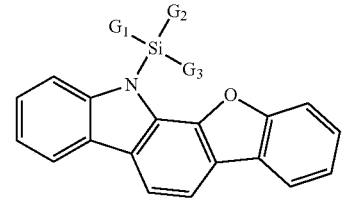
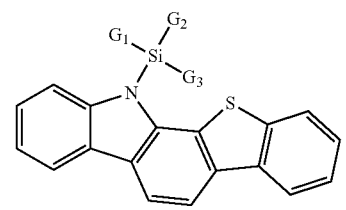
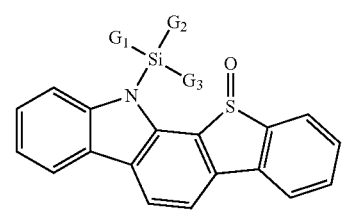
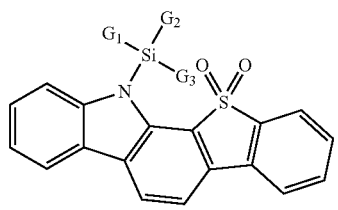

wherein each of $G_1$, $G_2$ and $G_3$ is selected from the group consisting of a hydrogen, and aromatic, heterocyclic and aliphatic groups which are optionally substituted.

2. The host material of claim 1, wherein the aromatic or heterocyclic groups are substituted with at least one selected from the group consisting of an alkyl group, an alkoxy group, a halogen group, a silyl group, a cyano group, deuterium, tritium and hydrogen.

3. The host material of claim 1, wherein the heterocyclic group includes 4-16 carbon atoms and at least one of 1-3 nitrogen atoms, 1-2 oxygen atoms and 1-2 sulfur atoms.

4. The host material of claim 1, wherein each of the $G_1$, $G_2$ and $G_3$ groups are represented by one of the following formulae:

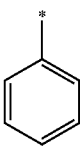
B1

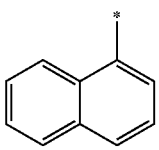
B2

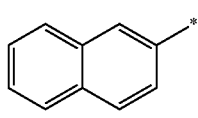
B3

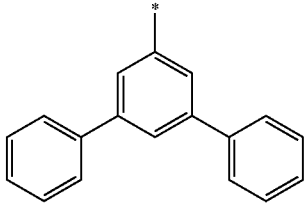
B4

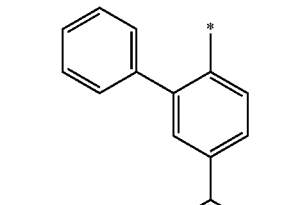
B5

B6 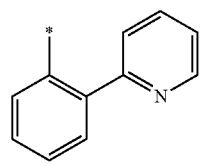
B7 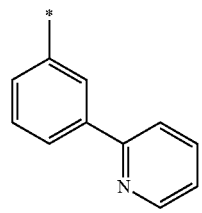
B8 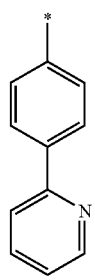
B9 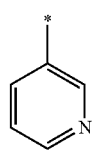
B10 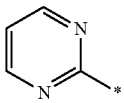
B11 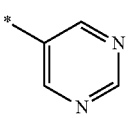
B12 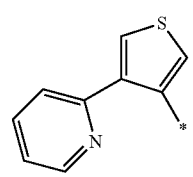
B13 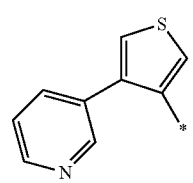
B14 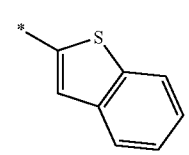
B15 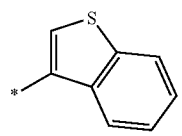
B16 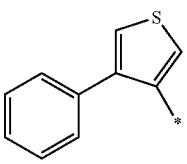
B17 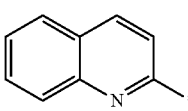
B18 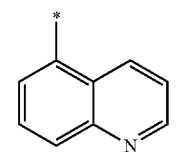
B19 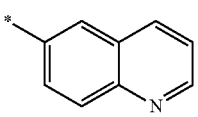
B20 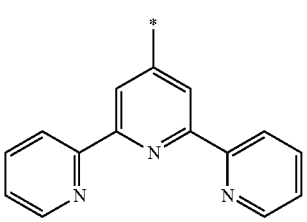
B21 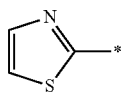
B22 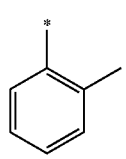
B23 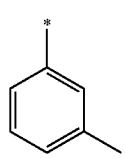
B24 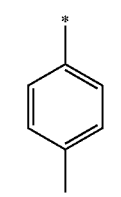

-continued
B25 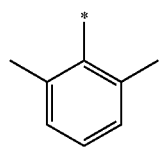
B26 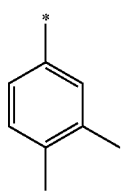
B27 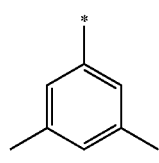
B28 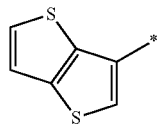
B29 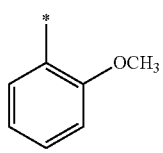
B30 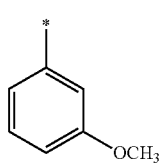
B31 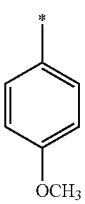
B32 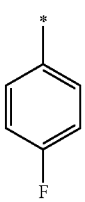
B33 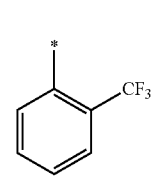
-continued
B34 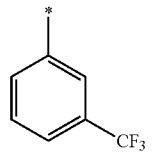
B35 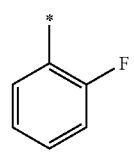
B36 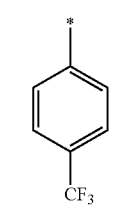
B37 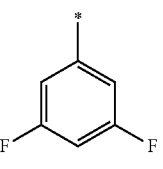
B39 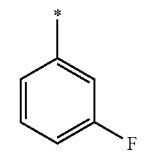
B40 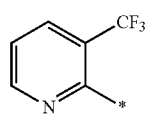
B41 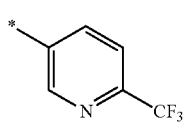
B42 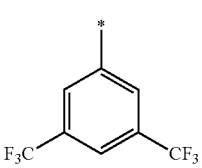
B43 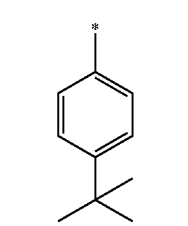

B44 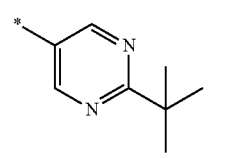
B45 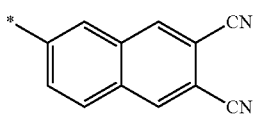
B46 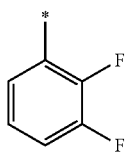
B47 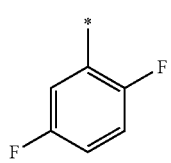
B48 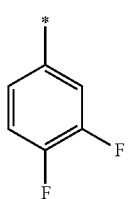
B49 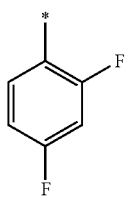
B50 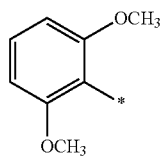
B51 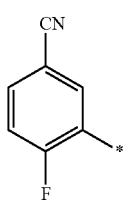
B52 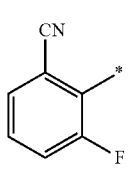
B53 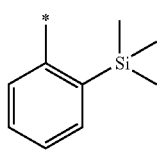
B54 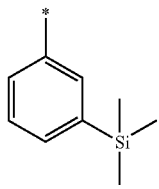
B55 
B56 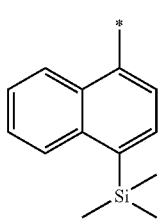
B57 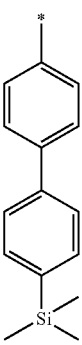
B58 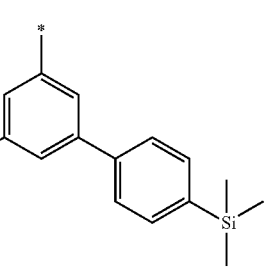
B59 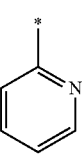

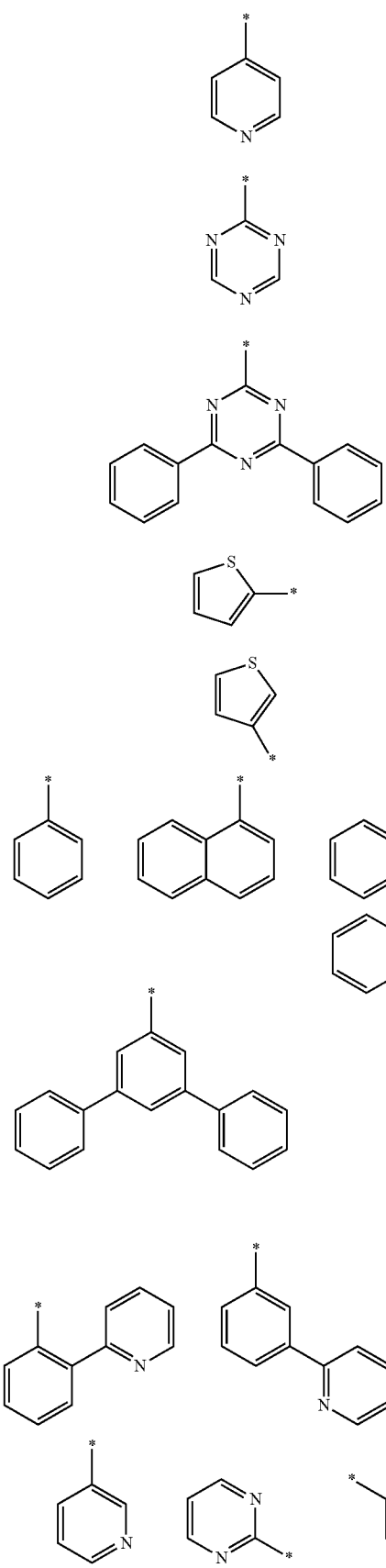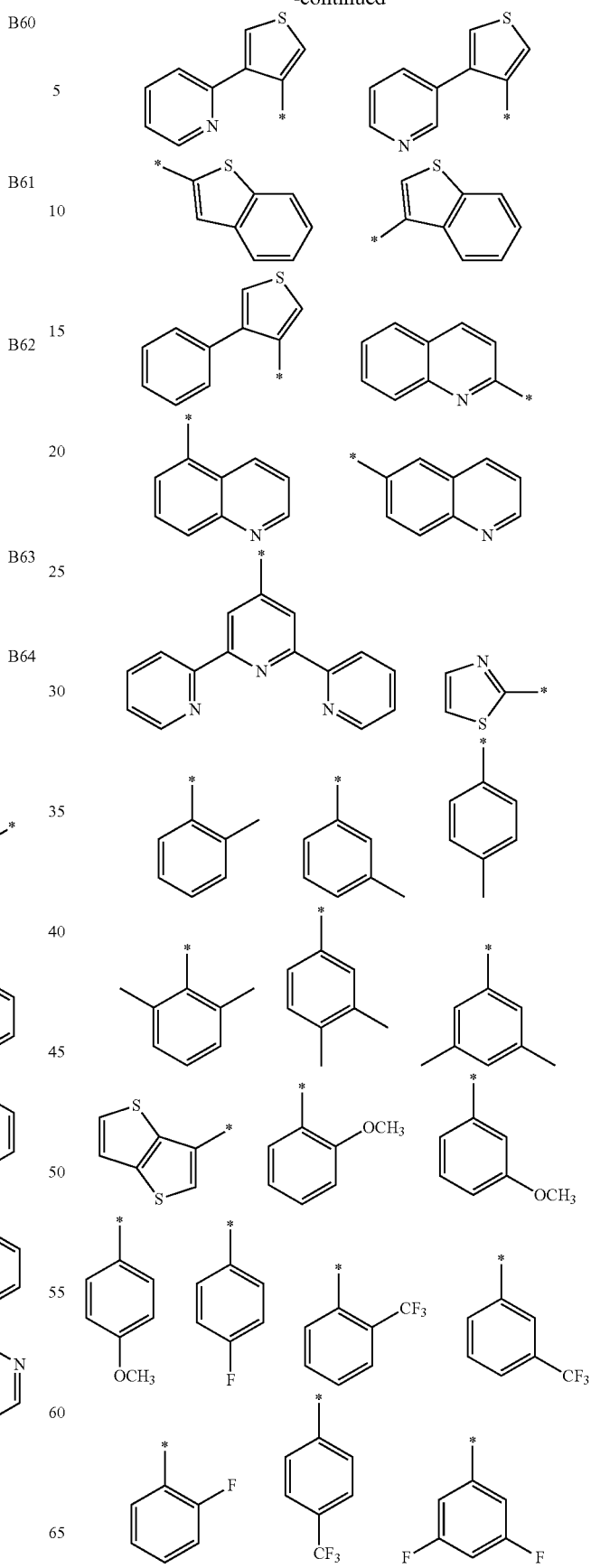

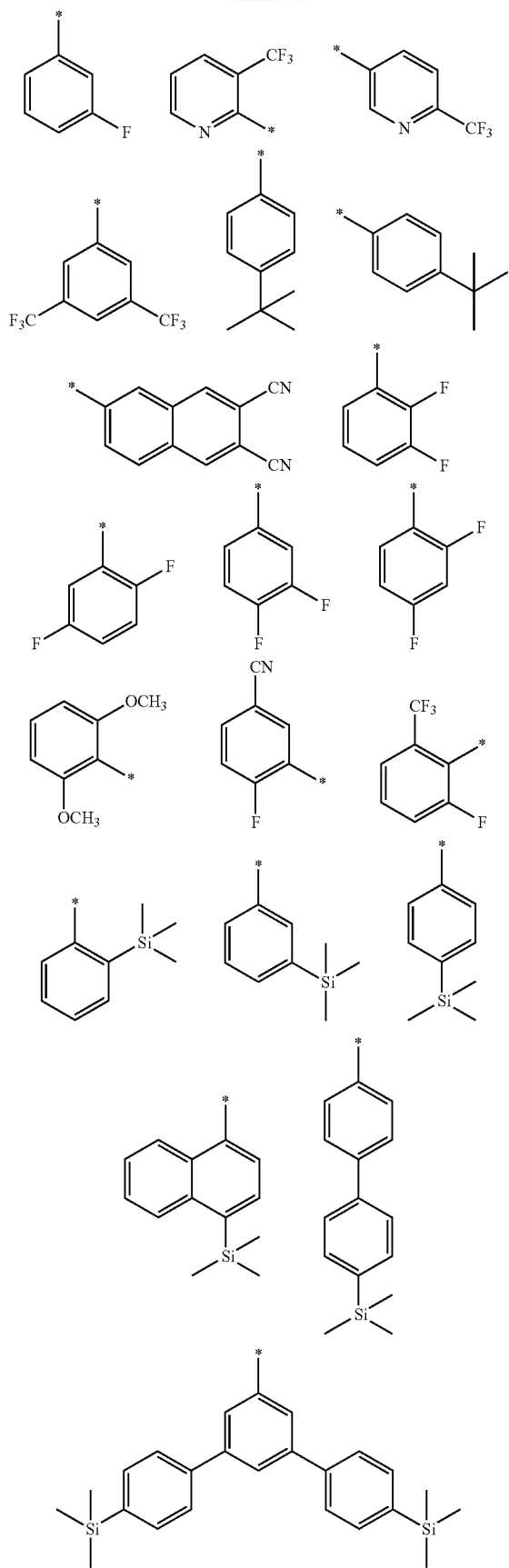
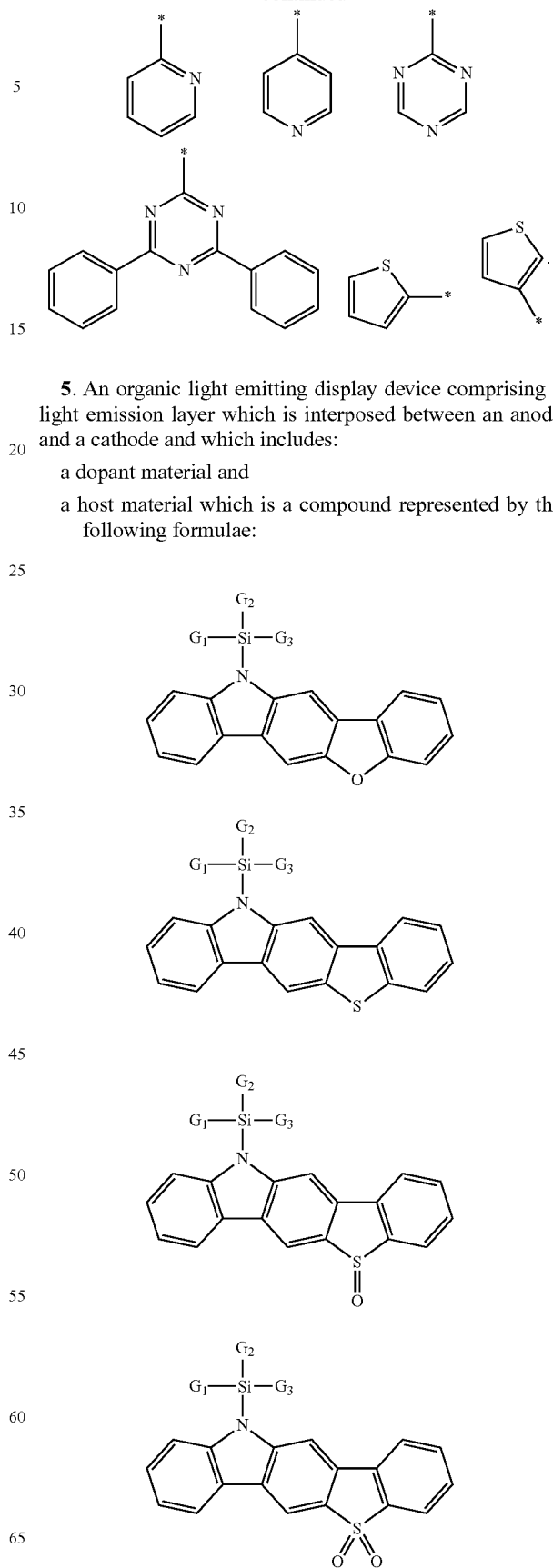
5. An organic light emitting display device comprising a light emission layer which is interposed between an anode and a cathode and which includes:
  a dopant material and
  a host material which is a compound represented by the following formulae:

-continued

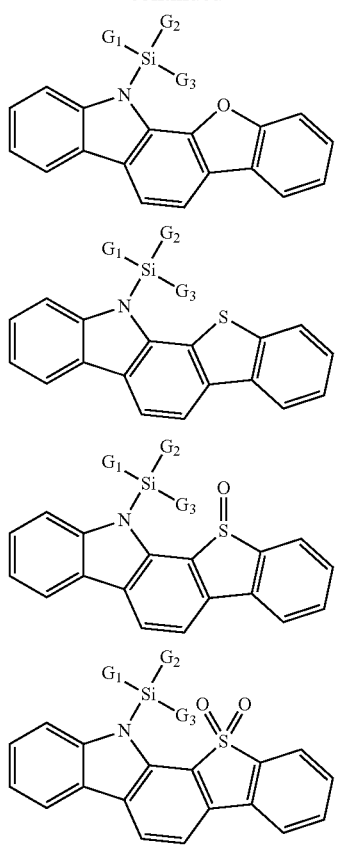

wherein each of G₁, G₂ and G₃ is selected from the group consisting of a hydrogen, and aromatic, heterocyclic and aliphatic groups which are optionally substituted.

6. The organic light emitting display device of claim 5, wherein the aromatic or heterocyclic groups are substituted with at least one substituent selected from the group consisting of an alkyl group, an alkoxy group, a halogen group, a silyl group, a cyano group, deuterium, tritium and hydrogen.

7. The organic light emitting display device of claim 5, wherein the heterocyclic group includes 4-16 carbon atoms and at least one of 1-3 nitrogen atoms, 1-2 oxygen atoms and 1-2 sulfur atoms.

8. The organic light emitting display device of claim 5, wherein each of the G₁, G₂ and G₃ groups are represented by one of the following formulae:

B1
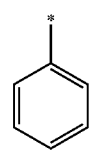

B2
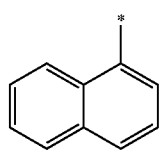

-continued

B3
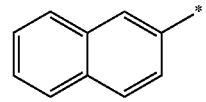

B4
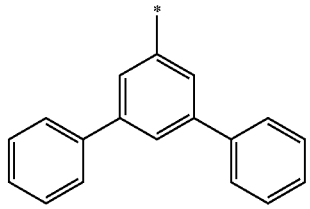

B5
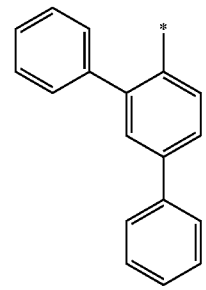

B6
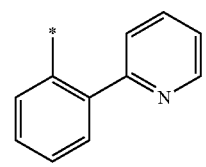

B7
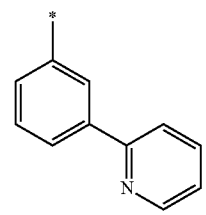

B8
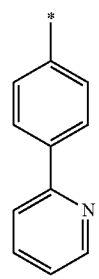

B9
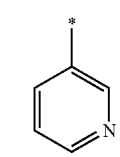

B10
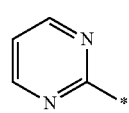

-continued
| | |
|---|---|
| 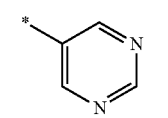 | B11 |
| 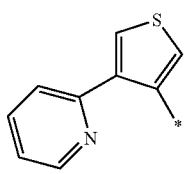 | B12 |
| 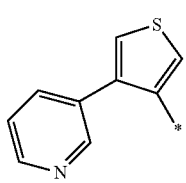 | B13 |
| 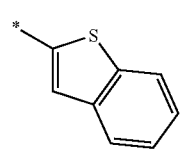 | B14 |
| 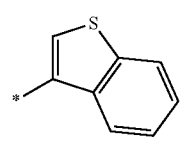 | B15 |
| 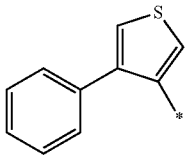 | B16 |
| 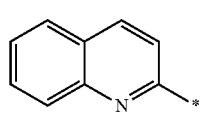 | B17 |
| 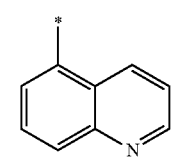 | B18 |
| 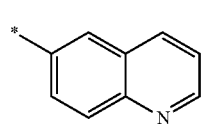 | B19 |
| 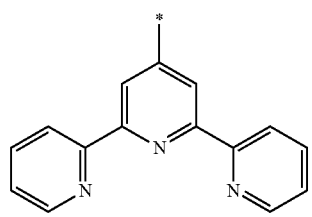 | B20 |
-continued
| | |
|---|---|
| 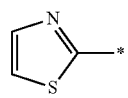 | B21 |
| 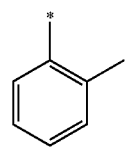 | B22 |
| 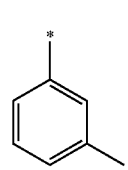 | B23 |
| 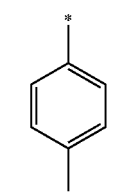 | B24 |
| 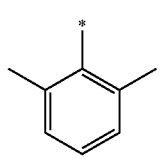 | B25 |
| 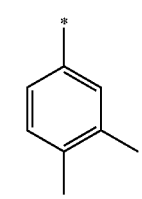 | B26 |
| 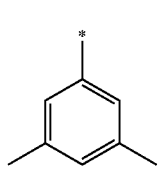 | B27 |
| 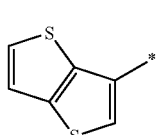 | B28 |
| 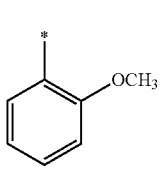 | B29 |
| 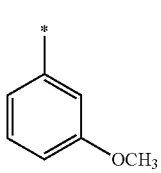 | B30 |

| | |
|---|---|
| 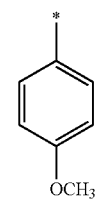 | B31 |
| 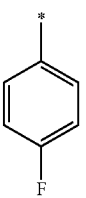 | B32 |
| 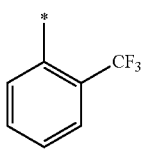 | B33 |
| 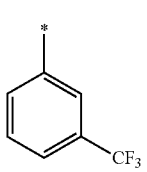 | B34 |
| 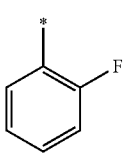 | B35 |
| 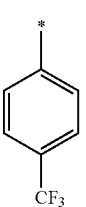 | B36 |
| 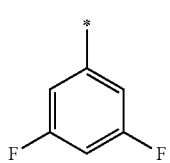 | B37 |
| 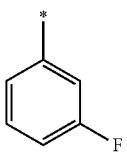 | B39 |
| 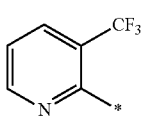 | B40 |
| | |
|---|---|
| 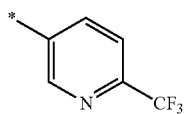 | B41 |
| 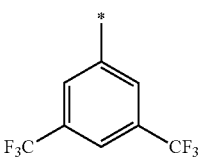 | B42 |
| 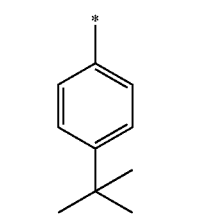 | B43 |
| 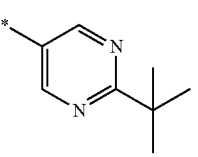 | B44 |
| 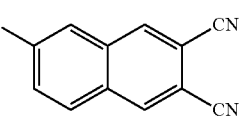 | B45 |
| 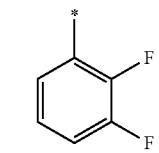 | B46 |
| 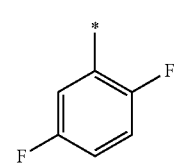 | B47 |
| 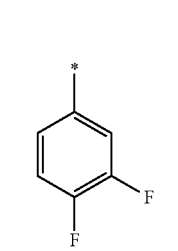 | B48 |
| 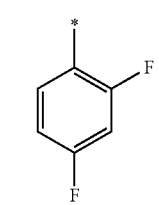 | B49 |

-continued
B50 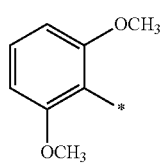
B51 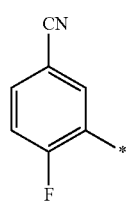
B52 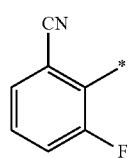
B53 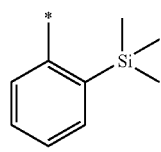
B54 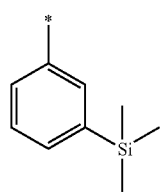
B55 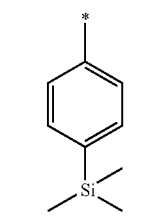
B56 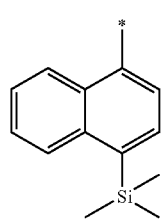
-continued
B57 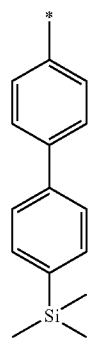
B58 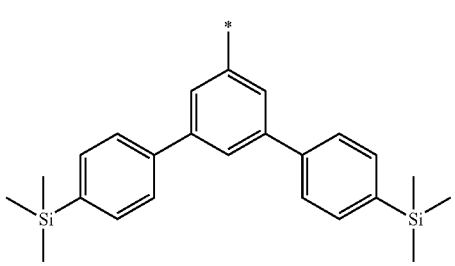
B59 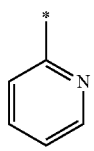
B60 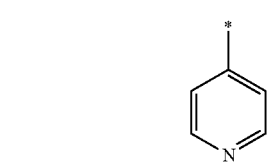
B61 
B62 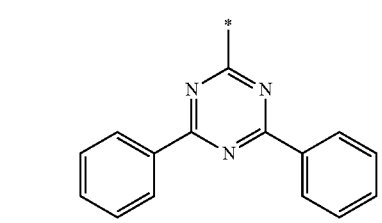
B63 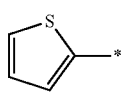
B64 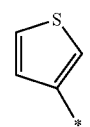

-continued
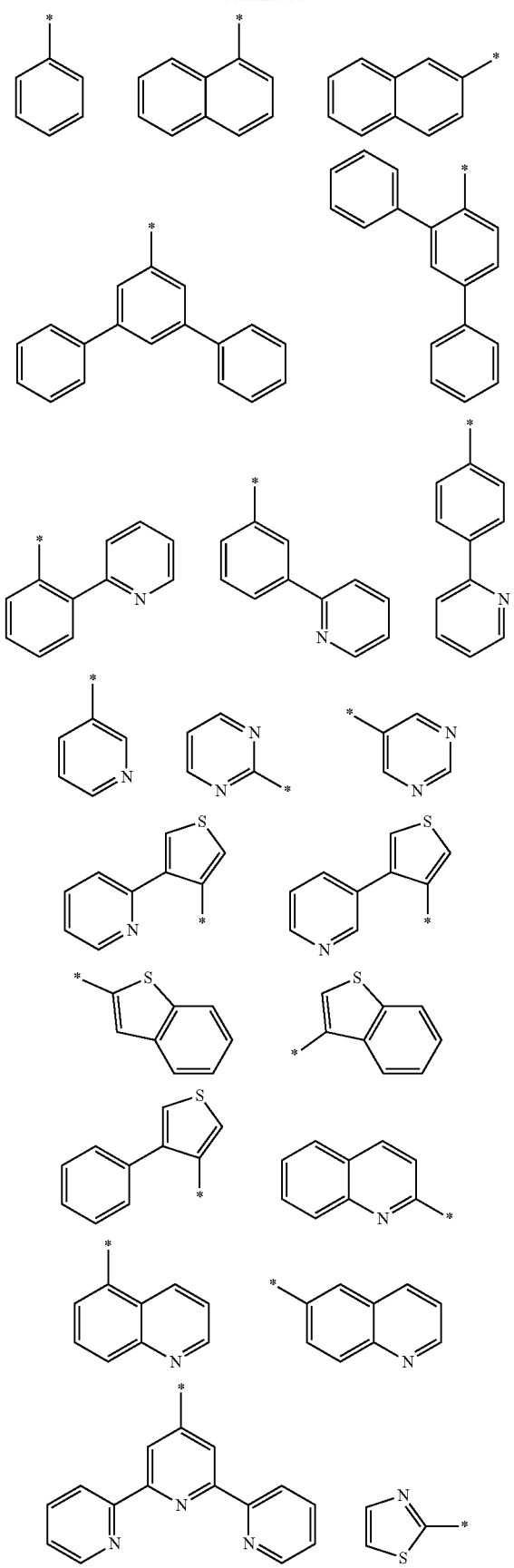
-continued
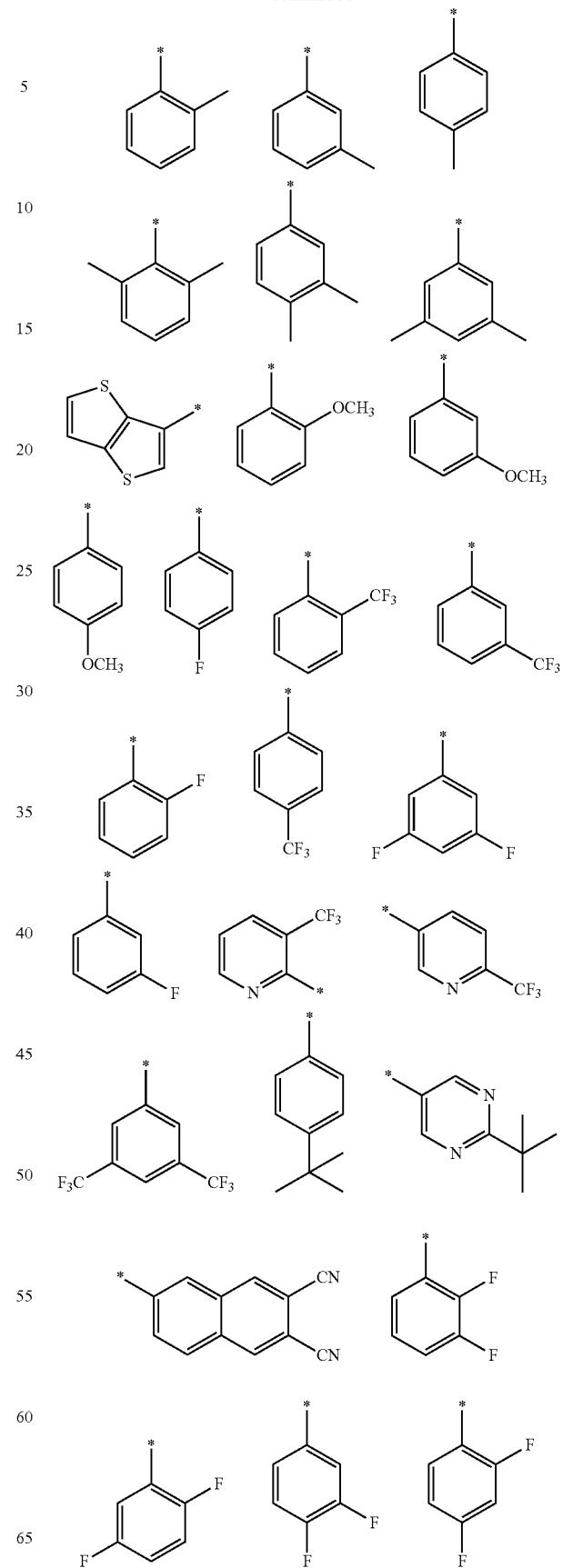

-continued

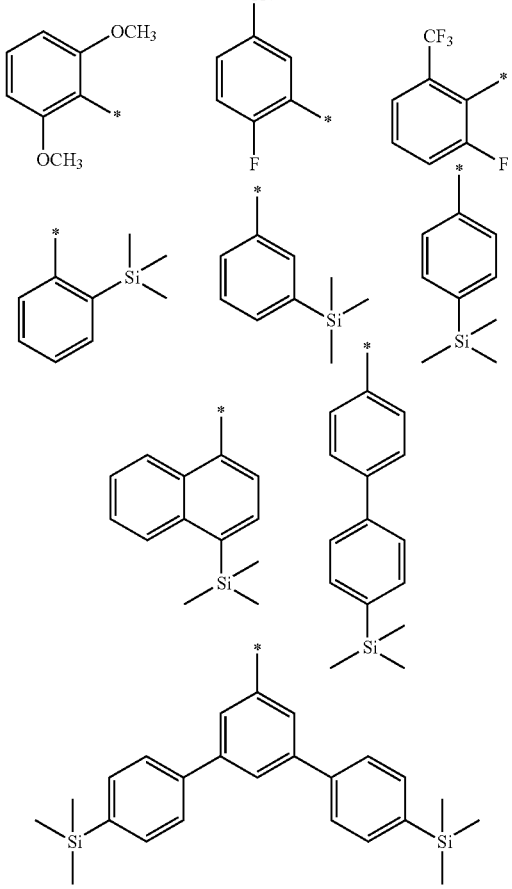
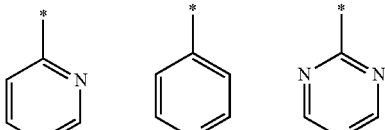

9. The organic light emitting display device of claim 5, wherein the dopant material is one of green and blue phosphorescent dopants.

10. The organic light emitting display device of claim 5, further comprising:

at least one of a hole injection layer and a hole transport layer which are interposed between the anode and the light emission layer; and at least one of an electron injection layer and an electron transport layer which are interposed between the light emission layer and the cathode.

* * * * *